United States Patent [19]

DePriest et al.

[11] 4,059,104

[45] Nov. 22, 1977

[54] APPARATUS, PROCESS AND PRODUCT

[75] Inventors: Donald R. DePriest; Bobby C. Brandon; Connell M. Buie, all of Columbus, Miss.

[73] Assignee: Humboldt Products Corporation, Columbus, Miss.

[21] Appl. No.: 654,869

[22] Filed: Feb. 3, 1976

Related U.S. Application Data

[62] Division of Ser. No. 549,892, Feb. 14, 1975, abandoned, which is a division of Ser. No. 362,451, May 21, 1973, Pat. No. 3,892,617.

[51] Int. Cl.$^2$ .............................................. A61B 19/06
[52] U.S. Cl. ................................................. 128/132 D
[58] Field of Search .................. 128/132 D, 292, 275

[56] References Cited

U.S. PATENT DOCUMENTS

| 3,236,370 | 2/1966 | Pereny et al. | 128/132 D |
|---|---|---|---|
| 3,856,006 | 12/1974 | Krzewinski | 128/132 D |
| 3,942,523 | 3/1976 | Rudtke | 128/132 D |

*Primary Examiner*—Lawrence W. Trapp
*Attorney, Agent, or Firm*—Beveridge, De Grandi, Kline & Lunsford

[57] ABSTRACT

Apparatus for manufacturing large disposable specialty drapes, particularly surgical drapes such as cystoscopy sheets and lithotomy sheets. Two strips of various stock material are automatically drawn to length from separate supplies, processed, and mated in the required configuration. The processing includes making of one or more fenestrations and, for those drapes requiring it, attachment of a filter. The material is then cut to length to provide the finished sheet. The work stations, at which the fenestrations are made, the filter attached, and the sheet cut, are spaced to permit these operations to be performed simultaneously on different sheets in a line. A control unit synchronizes and controls these operations. The finished sheet is provided with an improved filter which is attached to the sheet body by a heat sealing process, thus avoiding the separation of the filter due to excessive exposure to fluid in the course of a surgical procedure.

15 Claims, 10 Drawing Figures

FIG. 8
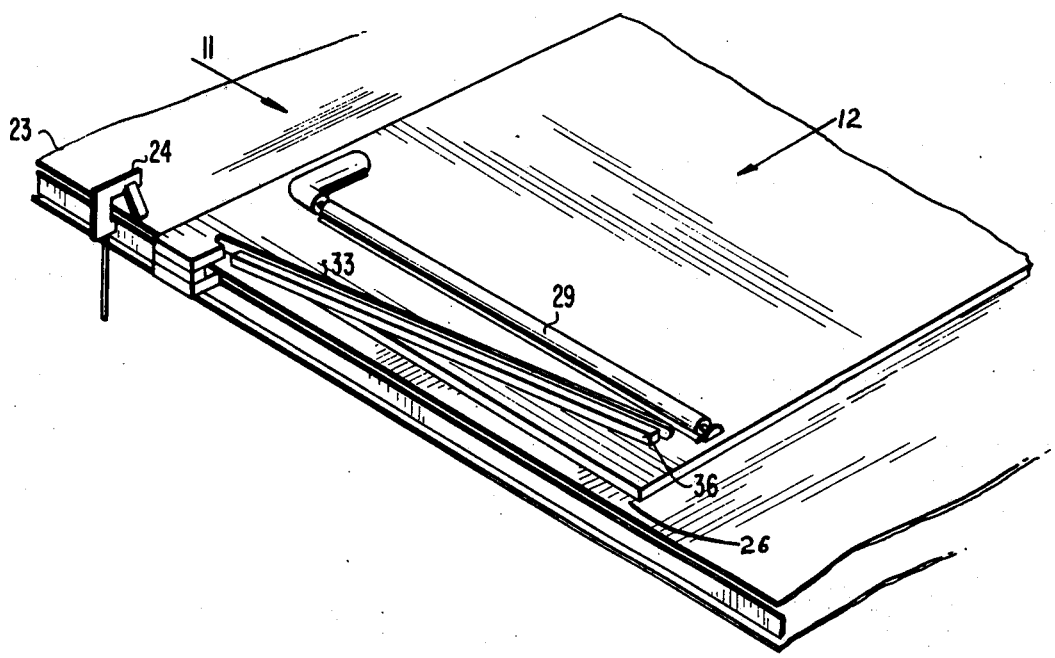
FIG. 9
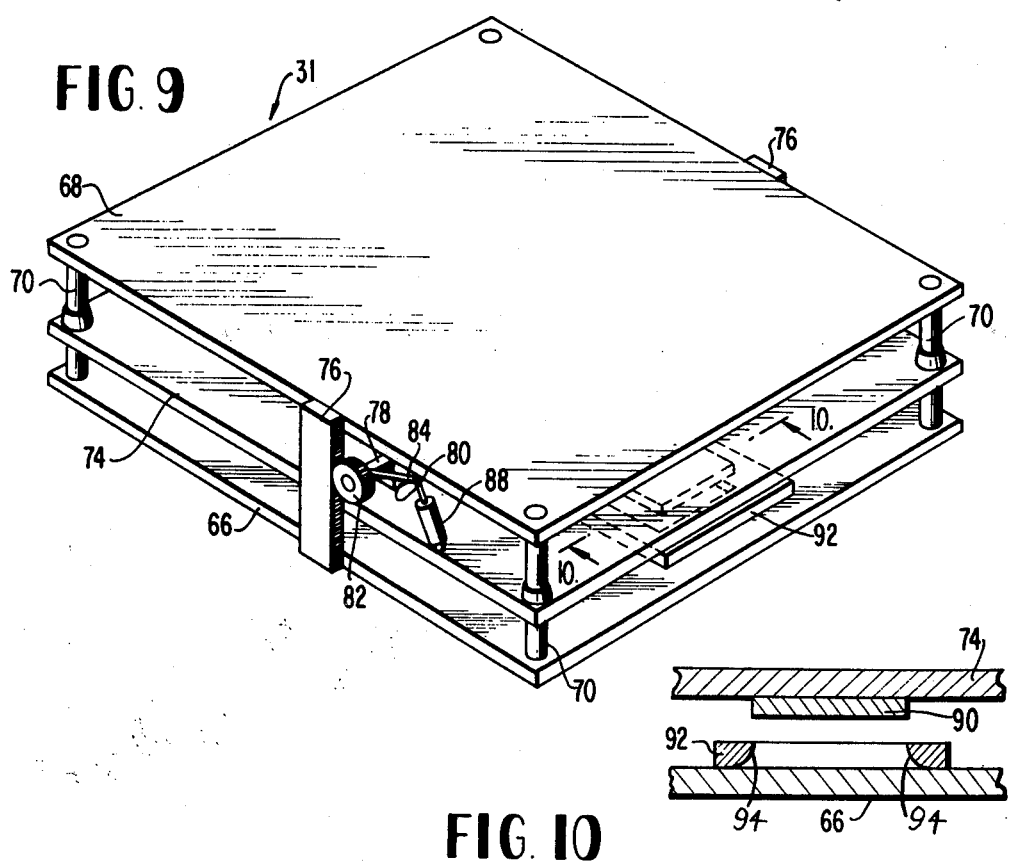
FIG. 10

APPARATUS, PROCESS AND PRODUCT

This is a division of abandoned application Ser. No. 549,892, filed Feb. 14, 1975 which in turn is a division of application Ser. No. 362,451, filed May 21, 1973, now U.S. Pat. No. 3,892,617.

The present invention pertains to large disposable specialty drapes. More particularly, it pertains to a process and an apparatus for manufacturing large disposable specialty drapes, such as cystoscopy sheets and lithotomy sheets, and to the resulting product.

Large disposable drapes or sheets are utilized in a variety of applications. By way of example, such drapes or sheets are used in hospital operating rooms to cover a patient undergoing surgery. These surgical drapes are provided in a variety of styles to meet the requirements of different operating procedures. The surgical sheets are generally provided with an opening or fenestration at a location determined by the surgical procedure involved. Surgical sheets used for operations such as the removal of gall stones, vaginal hysterectomy, or cystoscopy examination are generally shaped in the form of a "T". The patient generally reclines with raised knees, and the top section of the T-shaped sheets, referred to as the abdominal cover, is draped across the patient's torso, while the vertical section of the sheet, referred to as the T section, hangs between the patient's legs. In the T section, a fenestration is provided through which the surgical procedure is performed. Procedures such as cystoscopy or gall stone removal additionally require a filter in the T section to filter solids from the fluid passing from the patient. To accomodate this filter, a second fenestration is provided in the T section, and a fine screened filter is attached over this second fenestration. The sheet is formed of a fluid repellent material, at least in the T section area, and so the fluids which pass from the body during the surgical procedure flow over the sheet to the filter to pass therethrough. During such procedures, the filter is draped across a receptacle, and as the fluids pass through the filter, solids such as gall stones or other tissue are trapped in the filter for examination.

The fabrication of such large disposable sheets is complicated by the fact that the operating fenestration and the filter must be positioned quite exactly, and by the fact that the T section must be fluid repellent. Such sheets have been made in the past by cutting all the required pieces to size by hand, die-cutting the filter fenestration, both in the T section and in a reinforcement frame, attaching the T section substrate to the abdominal cover, placing the filter material over its fenestration, gluing the reinforcement frame to the T section to hold the filter therebetween, die-cutting the operating fenestration in that T section, and folding the sheet. In this prior art method, water base latex adhesives have been used to glue the filter and its reinforcement frame to the T section. These adhesives are water soluble and so tend to loosen during sustained exposure to fluids. This, of course, is undesirable, since it raises the possibility of the filter loosening in the course of the operating procedure. Further, in the past, the filter has been formed of material such as cotton gauze or a carded web. These materials, due to their inherent fibrous nature, exhibit a tendency to flake into the object of filtration. In addition, the coarseness of the weave of such material results in the filter having rather large and irregular interstices, necessitating the use of two or more plies to achieve the desired filtration.

Co-pending U.S. patent application Ser. No. 329,144, filed Feb. 2, 1973, by Donald R. DePriest and Bobby C. Brandon, discloses apparatus suitable for use in manufacturing large disposable drapes such as laparotomy sheets. Such sheets are generally rectangular and also have but one fenestration. Consequently, the apparatus and many of the techniques used in making laparotomy sheets, as disclosed in that patent application, are not capable of making other drapes such as cystoscopy and lithotomy sheets.

In a first aspect, the present invention is a process of and an apparatus for automatically manufacturing large disposable specialty drapes, particularly surgical drapes such as cystoscopy and lithotomy sheets, in which the number of manual steps is reduced to a minimum. In accordance with this aspect of the present invention, stock material is automatically fed through a series of work stations at which the necessary manufacturing operations are performed. In a second aspect, the present invention is a novel sheet produced by this process and apparatus. In this aspect, the present invention further includes a novel filtering arrangement using a polysheered monofilament material.

The apparatus of the present invention for forming large disposable drapes includes two sources of stock materials, preferably arranged at right angles to each other, and means for advancing stock material from each source to sequential work stations. The T section stock material is advanced to a first work station at which the one or two fenestrations are cut. The fenestrated material is then advanced to a second work station at which the T section is cut to the desired length and affixed to the abdominal cover stock material. If a surgical drape is being made which includes a filter, the filter and filter reinforcement frame are heat sealed to the T section over the filter fenestration at this second work station. During the time the T section stock material is moving to this second work station, abdominal cover stock material is advanced from its source to a work station aligned to place the abdominal cover stock material under the path of the advanced T section stock material. The alignment is arranged so that the abdominal cover stock material side edge to which the T section is to be attached is under the trailing edge of the portion of T section stock material which is at the T section second work station. The abdominal cover stock material at its first work station and the T section stock material at its second work station thus overlap. Means are provided at this location to cut the fenestrated T section with the filter attached thereto and to attach it to the abdominal cover stock material. This uncut abdominal cover stock material, with the cut T section attached, is advanced to a further work station at which the abdominal cover material is cut to the desired length to produce the finished surgical drape ready for folding. The various work stations of both stock materials are spaced so that the several operations can be performed simultaneously on different sheets in a line. In a preferred embodiment of this invention, a control unit is provided to synchronize and control movement of the stock material and several of the manufacturing operations simultaneously and automatically.

This invention is also directed to the novel drape produced by the process and apparatus of this invention and to a novel filter within the drape. The filter is attached by heat sealing techniques which eliminate the use of glue in areas subjected to draining fluids. The filter material is a woven synthetic monofilament material having improved filtering characteristics. The T section stock material and the filter reinforcement frame preferably are each a non-woven base material having laminated thereto a fluid impermeable material, such as polyethylene, polyurethane or polypropylene. As an example, one material suitable for use as the non-woven base material is a material having outer layers of cellulose wadding and inner layers of highly drafted fibers disposed angularly to each other, such as described in U.S. Pat. No. 3,484,330. Other suitable medical non-woven materials could, of course, be utilized. The T section and the filter reinforcement frame are heat sealed together, with the filter material therebetween. As a consequence, the finished drape has a superior filter with exceptional filering uniformity and filter life, and with no possibility of the filter loosening during the surgical procedure.

These and other aspects and advantages of the present invention are more apparent in the following detailed description and claims, particularly when considered in conjunction with the accompanying drawings. Like parts in the drawings bear like reference numerals. In the drawings:

FIG. 8 is a perspective view of a portion of the apparatus of FIG. 4;

FIG. 9 is a perspective view of a fenestration cutting device suitable for use in the apparatus of FIG. 4 in accordance with the present invention; and FIG. 10 is a fragmentary sectional view taken along line 10—10 of FIG. 9.

Figure 1:
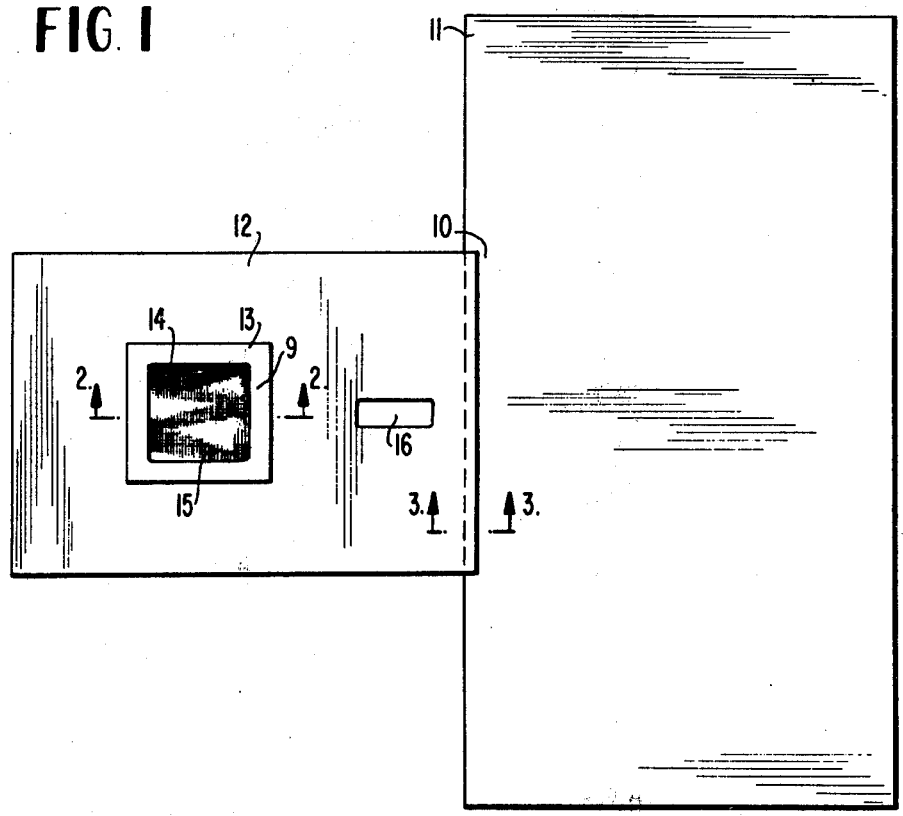
FIG. 1 is a plan view of a lithotomy sheet illustrative of the complex large disposable sheets or drapes of the present invention, and which may be manufactured by the process of and on the apparatus of the present invention.

FIG. 1 depicts a typical surgical drape such as a lithotomy sheet or T sheet 10 representative of complex specialty drapes manufactured in accordance with the present invention. Sheet 10 includes an abdominal cover section 11 and a T section 12. In the lithotomy drape 10 depicted in FIG. 1, T section 12 is provided with a filter 9, including filter reinforcement frame 13 and filter material 14, positioned at filtering fenestration or aperture 15 on T section 12. In addition, T section 12 is provided with operating fenestration 16. If a surgical drape is being formed which does not require a filter, for example a lithotomy sheet, then, of course, fenestration 15 is not made in T section 12, and filter reinforcement frame 13 and filter material 14 are not provided to omit filter 9. By way of example, sheet 10 might have an abdominal cover 11 with a width in the order of 72 inches and a length in the order of 44 inches, and might have a T section 12 with a width in the order of 28 inches and a length in the order of 44 inches. Sheet 10 may be provided with leggings extending from abdominal cover 11 on either side of T section 12, if desired, thus making the drape a one-piece cover for the patient undergoing the operation or examination. In this regard, the apparatus described below may be adapted to attach leggings to abdominal cover 11 in a manner similar to that used in applying T section 12 to cover 11. Alternatively, such leggings can be provided separate from sheet 10. The exact location of fenestration 16 and of filter 9 (if provided) might vary depending upon the exact surgical procedure with which sheet 10 is to be utilized.

Figure 2:
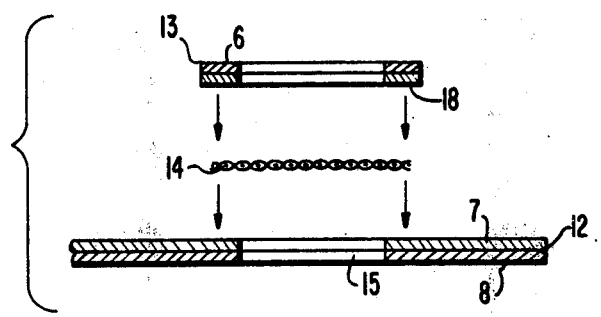
FIG. 2 is an exploded, fragmentary sectional view taken along line 2—2 of FIG. 1.
Figure 3:
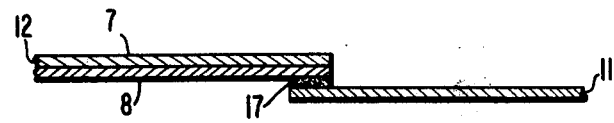
FIG. 3 is a fragmentary sectional view taken along line 3—3 of FIG. 1.
Figure 4:
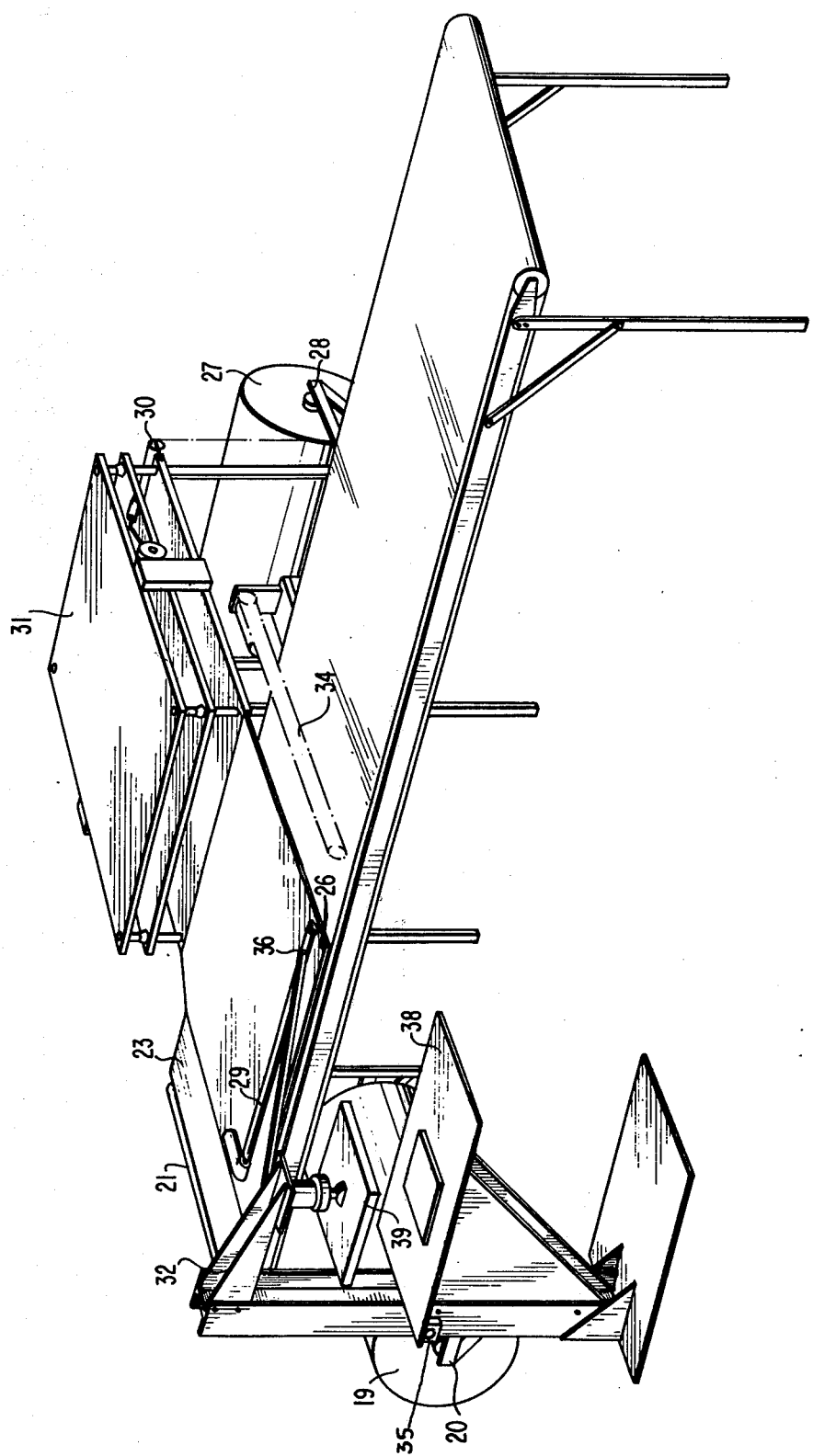
FIG. 4 is a perspective view of apparatus in accordance with the present invention for manufacturing the novel sheet of FIG. 1.
Figure 5:
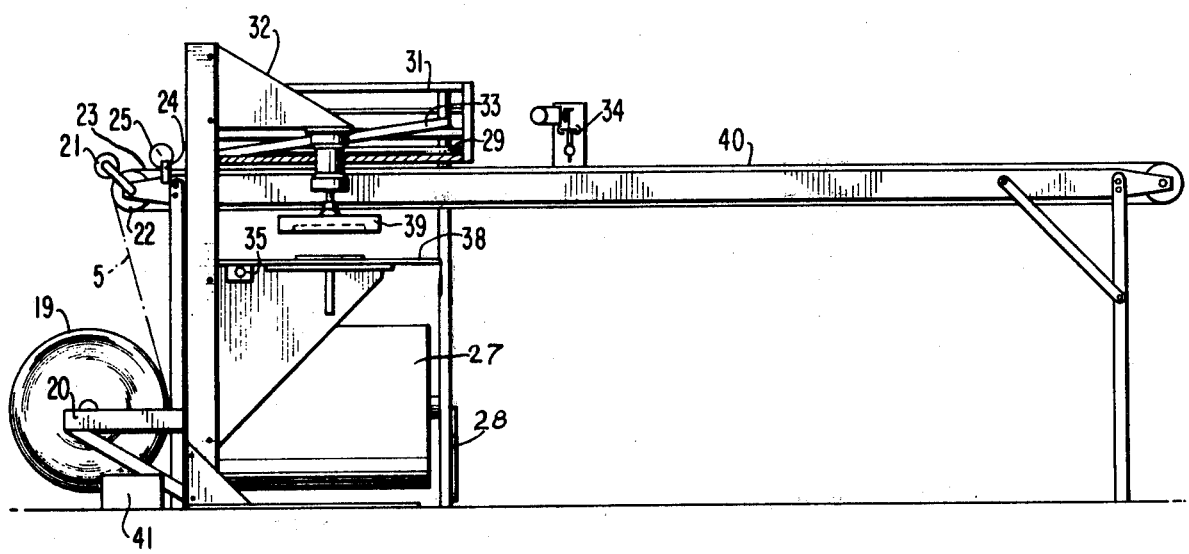
FIG. 5 is a side elevational view of the apparatus of FIG. 4.
Figure 6:
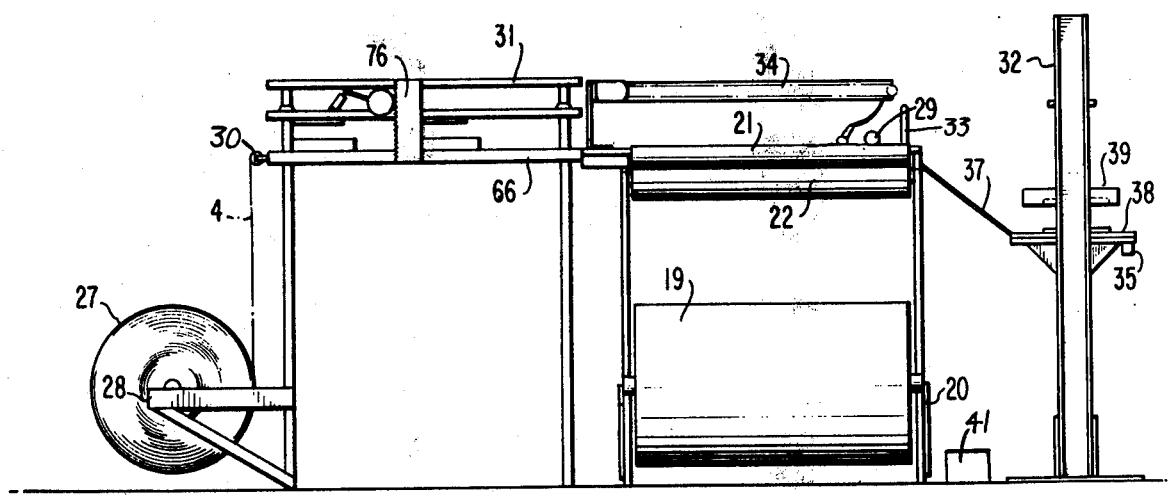
FIG. 6 is an end elevational view of the apparatus of FIG. 4.
Figure 7:
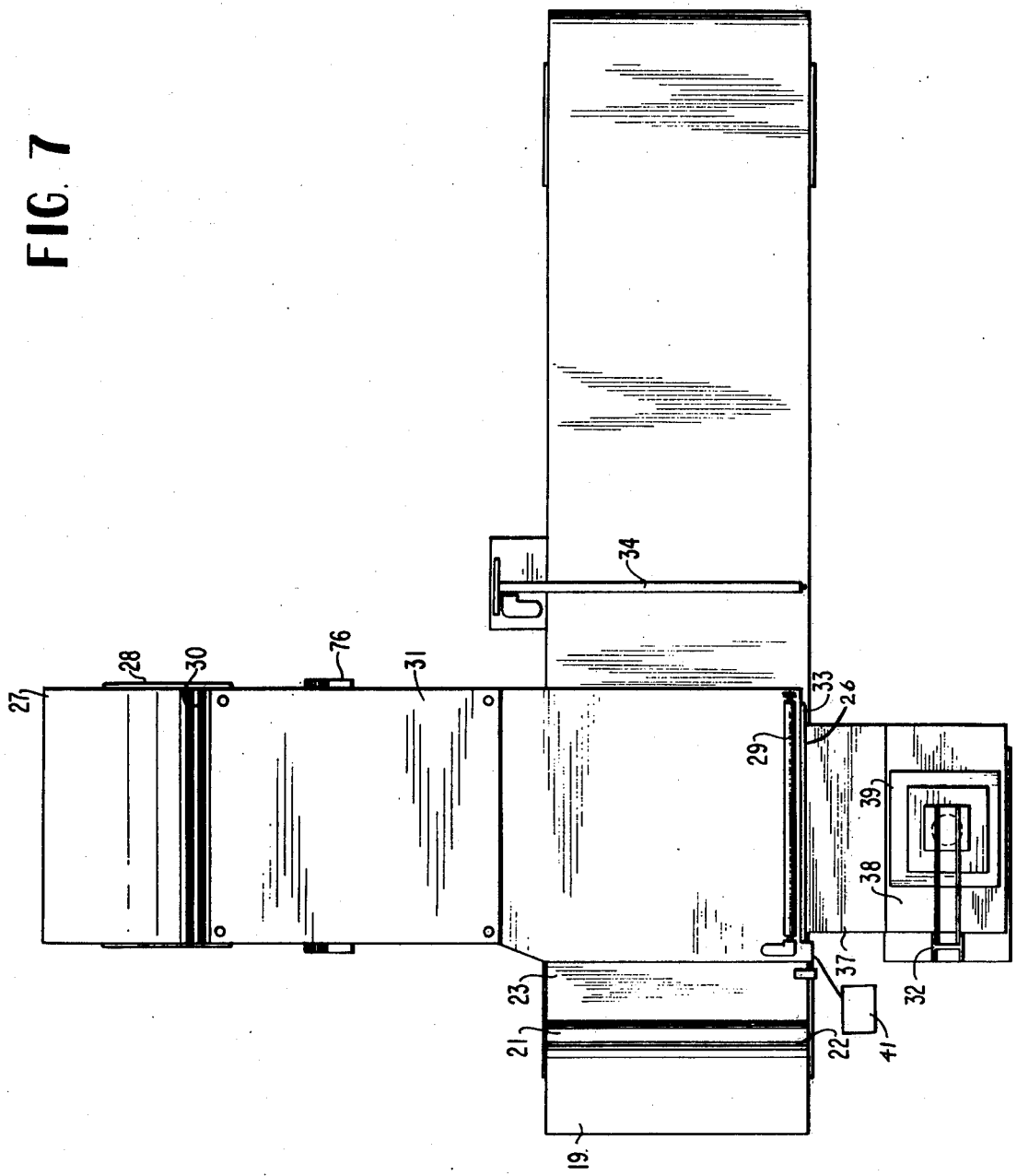
FIG. 7 is a top plan view of the apparatus of FIG. 4.

As seen in FIGS. 2 and 3, abdominal cover section 11 is preferably a non-woven material, suitably treated to be water-repellant, for example a material such as described in U.S. Pat. No. 3,484,330. T section 12 includes a first layer or substrate 8, which likewise is preferably a non-woven material, such as described in that same U.S. Pat. No. 3,484,330, suitably treated to be fluid repellant and having laminated thereto a second, fluid impermeable layer 7 of thermoplastic heat sealable material, such as polyethylene, polypropylene, or polyurethane. Filter reinforcement frame 13 likewise includes a first layer or substrate 6, preferably of a non-woven material, such as described in U.S. Pat. No. 3,484,330, suitably treated to be water repellant and having laminated thereto a second, fluid impermeable layer 18 of thermoplastic heat sealable material such as polyethylene, polypropylene, or polyurethane. Heat sealable layers 7 and 18 are preferably suitably treated to be anti-static.

FIGS. 1, 2, and 3 depict sheet 10 upside down; that is, in use during a surgical procedure, thermoplastic layer 7 and filter 9 are down, next to the patient. However, in accordance with the present invention, sheet 10 is manufactured with thermoplastic layer 7 and filter 9 up, as depicted in FIGS. 1, 2, and 3.

FIG. 2 illustrates the manner in which filter 9 is attached. T section 12 is positioned with its heat sealable layer 7 facing the heat sealable layer 18 of filter reinforcement frame 13, a filter material 14 is positioned between T section 12 and filter reinforcement frame 13. The filter material 14, filter frame 13 and T section 12 are brought into contact with each other and are fused together with heat about aperture 15 of T section 12. The interstices of filter material 14 permit suitable fusing of layers 7 and 18 through the filter materal.

Filter material 14 is a woven synthetic monofilament material having dimensions and characteristics defined by the type of filtering desired. One preferred filter material is polyester sheer, such as Fortrel or dacron having, for example, a 30 denier and a thread count in the order of from about 80 to about 120, and preferably about 100 per inch, in the warp direction and of from about 70 to about 105, and preferably about 90 per inch, in the fill direction. The interstices typically might be in the range of from about 0.006 to about 0.012 and preferably about 0.009 inches in the fill direction and alternately in the range of from about 0.008 to about 0.012, and preferably about 0.010 inches, and in the range of from about 0.002 to about 0.006 and preferably about 0.004 inches in the warp direction. The preferred monofilament has a very consistent diameter in the range of from about 0.001 inches to about 0.004 inches, and preferably about 0.002 inches. The sheer material thus has excellent regimentation of the weave and superior interstice uniformity. The material has a plain heat set finish, devoid of any silicone treatment which would tend to inhibit penetration of fluid. However, where needed, it may be surface treated with resin to completely inhibit absorption of moisture.

FIG. 3 illustrates the manner in which abdominal cover 11 and T section 12 are joined. Non-woven layer 8 of T section 12 is adhered to abdominal cover 11 by glue seam 17. Since fluid draining through fenestration 16 does not flow across the junction of T section 12 and abdominal cover 11, any suitable adhesive, such as a water base latex, may be used at glue seem 17.

FIGS. 4 through 10 illustrate one embodiment of apparatus for manufacturing complex specialty drapes in accordance with the present invention, for example surgical drapes such as cystoscopy sheet 10 of FIGS. 1-3.

Roll 19 contains stock material 5 for abdominal cover section 11, and is mounted on holder 20. Stock material 5 from roll 19 passes between pressure roller 21 and endless conveyor 23, which is advanced by power drum 22. Conveyor 23 carries the stock material past a first work or operating station at which glue head 24 applies adhesive to one edge of the stock material. Linear counter 25 measures linear progress of the stock material 5. Roll 27 contains stock material 4 for T sections 12, and is mounted on holder 28. Under the urging of power roller 29, stock material 4 from roll 27 passes, with its heat sealable layer upward, over roller 30 and through a first T section operating station at which is located a fenestrating or aperature cutting device 31. After operating fenestration 16 and, if desired, filter fenestration 15 have been made in stock material 4, the stock material advances to a second T section operating station where the individual T section 12 is cut from the fenestrated stock material, attached to stock material 5, and fused with filter material 14 and filter reinforcement frame 13. This second T section operating station is arranged to partially overlay the first abdominal section operating station so that stock material 4 passes over stock material 5 at substantially a right angle. At mating station 26, the trailing edge of the advancing T section 12, ready to be severed from stock material 4, is aligned above the edge of abdominal cover section 11 which is, as yet, unsevered from stock material 5. This abdominal cover section has had adhesive applied by head 24 to the edge which is to mate with the new T section 12.

A cutting blade 33 is positioned to sever the newly fenestrated T section 12 from stock material 4 with the new T section 12 lying on support 37 (shown only in FIGS. 6 and 7 for clarity) and across surface 38 of fusing station 32. As the new T section 12 is cut by cutting blade 33, pressure pad 36 presses the cut edge of the T section 12 into contact with the edge of the abdominal cover section 11 of stock material 5, having adhesive on it, forming glue seam 17. At the same time, an operator at fusing device 32 manually aligns filter material 14 and filter reinforcement frame 13, with its heat sealable layer downward, over filter fenestration 15 and then energizes control 35 to activate fusing device 32. Heated upper member 39 lowers to press against filter frame 13, fusing its heat sealable layer 18 with the heat sealable layer 7 of T section 12. Since filter material 14 has a large number of interstices, the heat sealing secures filter material 14 in place in a seal that is not loosened by fluid.

Upon completion of these simultaneous operations at this operating station, the stock material 5, with the now attached T section 12, advances to the next operating station at which automatic cutting knife 34 cuts the finished drape from the stock material 5. The finished drape is supported on surface 40 for folding and packaging.

Linear counter 25 measures linear progress of abdominal cover stock material 5. When the proper length of stock material 5 has been measured, linear counter 25 applies a signal to control unit 41 which controls operation of the apparatus. Control unit 41 stops power rollers 22 and 29 to stop withdrawal of stock materials 4 and 5. Control unit 41 also stops flow of glue from glue head 24. Stock material 4 is stopped with the newly fenestrated T section 12, positioned for cutting by blade 33. The portion of stock material 4 which is to be the next T section 12 is properly positioned at fenestration device 31 for the cutting of fenestration 16 and, if desired, fenestration 15. Control unit 41 then actuates cutting blade 33, fenestrating device 31, and automatic cutting knife 34 to cut an already fenestrated T section 12 to length, to fenestrate the next T section 12, and to cut a completely finished sheet 10. As cutting blade 33 separates a T section 12 from stock material 4, pressure pad 36 is actuated to press the edge of the newly severed T section 12 against the adhesive on the edge of abdominal cover stock material 5. Also, during this time, if a filter 9 is to be included in the finished sheet 10, an operator, as mentioned, positions filter material 14 and filter reinforcement frame 13 over filter fenestration 15 and then energizes control 35 to activate fusing device 32. Heated upper member 39 lowers to heat seal the filter. A time-delay relay incorporated in the control 35 deenergizes the fusing device 32 to raise member 39 after the proper dwell time, and automatically energizes control unit 41 to restart drive rollers 22 and 29 and glue head 24 for the next sheet. In addition to this synchronization, the several work stations are spaced so that their respective operations can be performed simultaneously on different sheets in a line.

FIGS. 9 and 10 show a fenestrating device suitable for use on fenestrating device 31. Lower member 66 and upper member 68 are fixedly mounted on rods 70. Center member 74 is slidingly mounted on rods 70 between lower member 66 and upper member 68. Racks 76 are mounted at the sides of cutting station 31 between lower member 66 and upper member 68. Shaft 78 is rotatably mounted to center member 74 by means of mounts 80. A pinion 82 is mounted on each end of shaft 78 to engage the racks 76. Linkage 84 couples shaft 78 to air cylinder 88 which is mounted on center member 74. Movement of linkage 84 under control of air cylinder 88 rotates shaft 78 to cause center member 74 to be raised or lowered. Other suitable means of raising and lowering member 74 could, of course, be provided.

A peened anvil punch press is positioned on center member 74 and lower member 66. Hammer member 90, shown in FIG. 10, is mounted on the lower surface of center member 74, while anvil member 92 is mounted opposite hammer member 90 and on the upper surface of lower member 66. Anvil member 92 includes beveled edges 94, while hammer member 90 has clean, non-beveled edges. Hammer member 90 is preferably of a hard steel, and anvil member 92 is preferably of a slightly softer metal. The stock material to be cut has a thickness in the order of a few mils. Anvil 92 might have a thickness in the order of 3 inches. Hammer 90 only goes into the opening of anvil 92 about ½ inch. Therefore, there are 2⅜ inches of depth in which the portions of material removed from stock material 4 can accumulate. This is generally enough catch room for a production run in the order of several hundreds of sheets. Alternatively, if desired, an opening can be provided in lower member 66 to conform with the outline of the opening through anvil member 92 so that the portion of the material removed as each fenestration is cut can fall from cutting station 31. However, with no opening through lower member 66, different hammers and anvils can be utilized to permit cutting different fenestrations for various types of surgical drapes and without weakening lower member 66. Cutting station 31 includes one or two sets of hammer 90 and anvil 92, depending upon whether both fenestrations 15 and 16, or only one of them, is to be made.

Cystoscopy sheets having the improved filter in accordance with the present invention provide improved filtering characteristics relative to prior art Cystoscopy sheets which have filters of, for example, gauze. The uniform quality of the filter, due to the regimentation of the interstices and uniformity of thread diameter, result in high quality and predictable filtering characteristics. The wetting characteristics of the synthetic monofilament enable the control of the point of filtering to assure that liquid passing through the filter is directed into a suitable receptacle. In contrast, cotton gauze filters of the prior art have non-uniform interstices, often making it necessary to double the gauze material. With such prior art filters, the liquid flow is often uncontrollable with the result that it pours onto the floor or the feet of the surgeon. This problem is aggravated when the liquid loosens the filter reinforcement frame, which in the prior art is generally glued to the sheet T section. Consequently, the present invention provides an improved sheet having improved filtering characteristics, as well as providing an apparatus for and/or process of manufacturing such sheets.

Although the present invention has been described with reference to a preferred embodiment, numerous modifications and rearrangements could be made, and still the result would be within the scope of the invention.

It is claimed:

1. A complex disposable specialty drape comprising:
   a. an abdominal cover section formed of a medical non-woven material rendered substantially fluid repellant;
   b. a T section formed of a medical non-woven material rendered substantially fluid repellant and having laminated thereto a fluid impermeable layer, said T section having a fenestration therein;
   c. adhesive means joining an edge of said T section to an edge of said abdominal cover section;
   d. a filter; and
   e. a filter reinforcement frame affixing said filter over said fenestration.

2. The drape of claim 1 wherein said fluid impermeable layer is selected from the group consisting of polyethylene, polyurethane and polypropylene.

3. A complex disposable specialty drape comprising:
   a. an abdominal cover section formed of a medical non-woven material rendered substantially fluid repellant;
   b. a T section formed of a medical non-woven material rendered substantially fluid repellant and having laminated thereto a fluid impermeable layer, said T section having at least two fenestrations therein;
   c. adhesive means joining an edge of said T section to an edge of said abdominal cover section;
   d. a filter; and
   e. a filter reinforcement frame affixing said filter over one of said fenestrations.

4. The drape of claim 3 wherein said fluid impermeable layer is a heat sealable material and in which said filter reinforcement frame is heat sealed to said T section non-woven material, with said filter between said T section non-woven material and said filter reinforcement frame.

5. The drape of claim 4 wherein said filter is a polyester sheer material.

6. The drape of claim 5 wherein said fluid impermeable layer is selected from the group consisting of polyethylene, polyurethane and polypropylene.

7. In a disposable surgical drape having a fenestration with a filter fastened over said fenestration, the improvement comprising forming the filter of a woven synthetic monofilament material.

8. The improvement of claim 7 in which the filter is formed of polyester sheer.

9. The improvement of claim 7 in which the filter has a thread count of from about 80 to about 120 per inch in the warp direction and a thread count of from about 70 to about 105 per inch in the fill direction.

10. The improvement of claim 9 in which the filter has a thread count of about 100 per inch in the warp direction and a thread count of about 90 per inch in the fill direction.

11. The improvement of claim 7 in which the woven synthetic monofilament material is formed of a monofilament having a diameter of from about 0.001 to about 0.004 inch.

12. The improvement of claim 11 in which the diameter is about 0.002 inch.

13. The drape of claim 1 wherein said fluid impermeable layer is a heat sealable material and in which said filter reinforcement frame is heat sealed to said T section non-woven material, with said filter between said T section non-woven material and said filter reinforcement frame.

14. The drape of claim 13 wherein said filter is a polyester sheer material.

15. The drape of claim 14 wherein said fluid impermeable layer is selected from the group consisting of polyethylene, polyurethane and polypropylene.

* * * * *